United States Patent [19]

Suggitt et al.

[11] 3,960,964

[45] June 1, 1976

[54] HYDROCARBON UPGRADING PROCESS

[75] Inventors: Robert M. Suggitt, Wappingers Falls; Walter C. Gates, Jr., Newburgh; Ralph B. Hudson, Jr., Beacon, all of N.Y.

[73] Assignee: Texaco Inc., New York, N.Y.

[22] Filed: Dec. 13, 1974

[21] Appl. No.: 532,354

Related U.S. Application Data

[62] Division of Ser. No. 428,508, Dec. 26, 1973.

[52] U.S. Cl. .......................... 260/583 M; 208/144; 208/145; 252/438; 260/639 B; 260/644; 260/676 R
[51] Int. Cl.² ........................................ C07C 85/11
[58] Field of Search ................... 260/583 M, 676 R; 208/145, 144; 252/438

[56] References Cited
UNITED STATES PATENTS

| 3,322,843 | 5/1967 | Frandolig et al. ............... 260/676 R |
| 3,470,252 | 9/1969 | Doyle et al. .................... 260/583 M |

*Primary Examiner*—Arthur P. Demers
*Attorney, Agent, or Firm*—T. H. Whaley; C. G. Ries; George J. Darsa

[57] ABSTRACT

A process for converting mixtures of $C_6$ to $C_{30}$ n-paraffin and n-paraffin by-products to substantially pure n-paraffin which comprises catalytically hydrogenating the mixture at a temperature of from about 600° to 750°F. in the presence of a Group VIII metal on alumina catalyst, and from about 10 to 5,000 parts per million of nitrogen present as ammonia or an organonitrogen compound. The catalyst can additionally contain a Group VIB or VIIB metal.

11 Claims, No Drawings

HYDROCARBON UPGRADING PROCESS

This is a division, of application Ser. No. 428,508, filed Dec. 26, 1973 now U.S. Patent 3,949,012.

This invention relates to a process for converting mixtures containing n-paraffins to substantially pure n-paraffins. In particular this invention relates to a process for converting mixtures of $C_6$ to $C_{30}$ n-paraffins and $C_6$ to $C_{30}$ by-products to substantially pure $C_6$ to $C_{30}$ n-paraffins by catalytic hydrogenation.

Normal paraffin hydrocarbons having from 6 to 30 carbon atoms represent valuable feedstock materials which can be converted to highly desirable products including amines by nitration and hydrogenation or to oximes by photonitrosation or to secondary alcohols by oxidation. In the illustrative processes described above, from about 5 to 50 weight percent of the normal paraffin undergoes conversion which results in the formation of a crude product mixture containing not only the desired material and unconverted paraffin but additionally substantial amounts of oxygenated paraffin by-products which can in some instances be produced in equal quantities with the sought after product. The desired product, for example, the amine or oxime or secondary alcohol is separated and recovered from the crude reaction product leaving a raffinate composed of a mixture of n-paraffin and oxygenated n-paraffin. While the raffinate may be recycled for further conversion to the preselected product, the presence of the oxygenated compounds present innumerable problems including the substantial buildup of undesired by-products and the further conversion of the oxygenated hydrocarbons to multifunctional materials. The formation and buildup of substantial amounts of by-products in turn seriously reduces the attractiveness and selectivity of the process which ultimately leads to a highly unsatisfactory and cost prohibitive operation.

Heretofore, the n-paraffins contained in the mixture have been purified employing various procedures including the use of molecular sieve selective adsorbents to provide streams suitable for recycle substantially free of contaminants. However, this procedure is objectionable in that it removes substantial amounts of paraffin by-products, which by-products must be ultimately disposed of. This operation is particularly costly where by-product formation approximates the amount of desired product originally formed. Other techniques involved upgrading the mixture of hydrogenating crude normal paraffin mixtures containing oxygenated paraffins at temperatures of from about 450° to 600°F. in the presence of previously disclosed hydrogenation catalysts. However, even at this temperature range some hydrocracking to light paraffins and hydrogenolysis to methane occurred leading to losses in recoverable recycle material. Further, temperatures in excess of 600°F. were to be avoided as the same caused excessive undesirable isomerization, hydrocracking, hydrogenolysis and coking of the hydrocarbons to, for example, isoparaffins and methane. While hydrogenation of the crude mixture at 450° to 600°F. is not particularly effective inasmuch as some hydrocracking and isomerization occurs which reduces the amount of valuable feedstock which can be recycled, the oxygenated by-products are only partially hydrogenated such that a considerable amount of incompletely converted by-products are recycled.

It is therefore an object of this invention to provide a process which provides substantially pure n-paraffins from mixtures of n-paraffin and oxygenated paraffin hydrocarbons in high yields.

Another object of this invention is to provide a process for converting a mixture of n-paraffin and oxygenated paraffin to substantially pure n-paraffin.

Yet another object of this invention is to provide a process wherein mixtures of n-paraffins and oxygenated paraffin hydrocarbons are continuously converted to pure n-paraffin compositions.

Other objects and advantages will become apparent from a reading of the following detailed description and examples.

SUMMARY OF THE INVENTION

Broadly this invention contemplates a process for converting a mixture of n-paraffin and n-paraffin by-products, that is, oxygenated paraffin, to substantially pure n-paraffin which comprises catalytically hydrogenating the mixture at a temperature of from about 600° to 750°F., preferably from 610° to 700°F., in the presence of a catalyst composed of alumina and a Group VIII metal, and from about 10 to 5,000, preferably 100 to 3,000, parts per million of nitrogen present as ammonia or an organonitrogen compound basis the paraffin mixture. The catalyst can also contain as a component thereof an oxide of a member from Group VIB or a member from Group VIIB.

The catalyst employed in our process is one which comprises a member of Group VIII of the Periodic Table and alumina. Exemplary of the Group VIII metals are platinum, palladium, rhodium and ruthenium. Nickel and cobalt are also contemplated preferably in combination with a Group VIB metal oxide such as molybdenum oxide or tungsten oxide. A Group VIIB member such as rhenium present as the metal can also be used in combination with the Group VIII metal. Aluminas in various forms may be used as a component of the catalyst and particularly those aluminas having replaceable surface hydroxyl groups and surface areas of from 50 to 400 square meters per gram using the BET method. Included within our definition of alumina we mention, for example, eta-alumina, gamma-alumina, silica stabilized aluminas, i.e., aluminas containing up to approximately 5 weight percent $SiO_2$, thoria-alumina, zirconia-alumina, titania-alumina and chromia-alumina. The Group VIII metal is present in amounts ranging from about 0.1 to 5.0 weight percent, preferably from about 0.1 to 2.0 percent, for the noble metals and from 1 to 5 percent for nickel and/or cobalt, based on the composite catalyst. The Group VIB metal oxide component when present ranges from about 5 to 20 percent of the composite catalyst. The Group VIIB metal can be present in an amount of from about 0.1 to 2.0 weight percent.

The catalyst described above is made selective in converting the mixture of n-paraffin and oxygenated paraffin to substantially pure n-paraffin at a temperature of from about 600° to 750°F. by the presence of 10 to 5,000, preferably 100 to 3,000, parts per million of nitrogen present as ammonia or an organonitrogen compound basis the paraffin mixture.

As set out above, the catalyst employed in the instant process is made selective by the presence of the recited amount of ammonia or an organonitrogen compound. Suitable organonitrogen compounds include monoalkylamines such as methylamine, ethylamine, propylamine, butylamine, isobutylamine and pentylamine; dialkylamines such as dimethylamine, diethylamine, methylethylamine, dipropylamine, dibutylamine, dipentylamine; trialkylamines such as trimethylamine, triethylamine, methyldiethylamine, tripropylamine, tributylamine, tripentylamine; nitriles such as acetonitrile, acrylonitrile and methacrylonitrile; and alkenylpolyamines such as ethylene diamine, propylene diamine, diethylene triamine, dipropylene triamine, triethylene tetramine and tripropylene tetramine. The compounds employed to moderate the catalyst include those selected from the group consisting of:

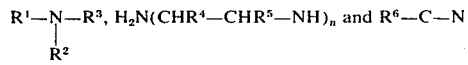

where $R^1$, $R^2$ and $R^3$ are hydrogen or alkyl of from 1 to 5 carbons; $R^4$ and $R^5$ are respectively hydrogen or hydrogen and methyl and where n is from 1 to 3; and where $R^6$ is hydrogen, alkyl of from 1 to 5 carbons or alkenyl of from 2 to 5 carbons.

The presence of the nitrogen compound moderates the activity of the Group VIII metal on alumina catalyst which in the absence thereof and at hydrogenation temperatures of from about 600° to 750°F. otherwise causes substantial isomerization and hydrocracking of the mixture to isoparaffins and light paraffins. The presence of the ammonia or nitrogen compound deters isomerization and hydrocracking of the mixture including the n-paraffin and by-products and thereby selectively converts the by-products to valuable n-paraffin recycle feedstock.

The catalyst described above can be prepared by introducing the Group VIII metal, and when desired the Group VIB or VIIB member, to the alumina by impregnating with an aqueous solution of a soluble salt of the metal followed by drying and calcination at a temperature of from 600° to 1200°F. for several hours.

The alumina component of the catalyst complements the hydrogenating activity of the Group VIII metal by promoting the dehydration of alcohols or glycols present to the corresponding olefin which are in turn hydrogenated to n-paraffin. This property of the catalyst is particularly beneficial not only at the operative hydrogenation temperature range of from 600° to 750°F., but the dual functional aspect of the catalyst is particularly advantageous in converting any olefinic material formed at the elevated temperatures and partially converted to n-paraffin to be essentially converted to n-paraffin by an additional and subsequent hydrogenation undertaken at about 450° to 650°F.

In some instances it may be desirable to pass the recycle mixture through a bed of alumina, silica gel or activated carbon to act as guard case for the hydrogenation catalyst. Illustratively, a recycle mixture derived from the conversion of paraffins to secondary alcohols will contain minor amounts of boric acid and borate esters which adversely affect hydrogenation catalysts. Such materials can be effectively removed from the mixture prior to hydrogenation by, for example, passing the mixture at 400° to 500°F. through a bed of activated alumina.

As mentioned above, an additional and subsequent hydrogenation may also be desirable as, for example, when the liquid product hydrogenated at 600° to 750°F. is found to contain minor amounts of $C_6$ to $C_{30}$ olefins. Such an additional hydrogenation treatment can be conducted at from about 450° to 650°F. wherein the olefin is converted to n-paraffin employing catalysts of the type described in connection with the hydrogenation at 600° to 750°F.

In general, hydrogenation is undertaken in the presence of hydrogen at pressures ranging from about 100 to 1500 p.s.i.g. for periods of from 0.2 to 5 hours. In continuous processing the mixture can be introduced at space velocities of from 0.2 to 10.0 volumes of liquid feed per volume of catalyst per hour (v./v./hr.).

The mixtures hydrogenated according to the instant invention and composed of n-paraffins having from 6 to 30 carbon atoms and n-paraffin by-products, that is, oxygenated paraffins having from 6 to 30 carbon atoms can be derived from a plurality of sources. Typically, the mixture contemplated for hydrogenation in accordance with the instant invention is predominantly $C_6$ to $C_{30}$ n-paraffin containing from 0.5 to 30 weight percent oxygenated paraffins. Representative of the $C_6$ to $C_{30}$ oxygenated paraffins are alcohols, ketones and polyoxygenated materials such as acids, esters, glycols, lactams, ketoacids, and ketoalcohols. The mixture depending upon its source can also contain additional materials capable of being converted to normal paraffins in the presence of the catalyst described above and under the hydrogenation conditions recited. Among such materials are included $C_6$ to $C_{30}$ alkylchlorides and olefins.

Illustrative of the sources of the mixtures hydrogenated herein we mention the following. In the production of secondary alkyl primary amines from n-paraffins having from 6 to 30 carbon atoms, the amines are prepared by nitrating from about 5 to 50 weight percent of the paraffin to nitroparaffin employing as nitrating agent, for example, nitric acid, nitrogen dioxide or dinitrogen tetroxide at a temperature of from about 250° to 500°F. to form a crude nitrated product containing in addition to unconverted n-paraffin and nitroparaffin substantial quantities of oxygenated by-products such as $C_6$ to $C_{30}$ ketones, alcohols, carboxylic acids, nitrites, nitrates and multifunctional materials such as dinitroparaffins, nitroalcohols, nitroketones and ketoalcohols. Thereafter the crude nitrated liquid product typically comprising from 50 to 94.5 weight percent unreacted n-paraffin, 5 to 35 weight percent nitroparaffin and 0.5 to 15 weight percent oxygenated by-products is introduced to a hydrogenation zone where the nitroparaffin is essentially completely hydrogenated to the amine at conversion temperatures ranging from over 350° to 500°F. in the presence of conventional and well known hydrogenation catalysts. A preferred catalyst is palladium on carbon. The crude liquid hydrogenated product comprises $C_6$ to $C_{30}$ n-paraffin secondary alkyl primary amine and oxygenated by-products such as acids, alcohols, ketones, ketoalcohols, aminoalcohols and aminoketones. Other by-products such as secondary amines and diamines can also be present. The amines are separated from the liquid hydrogenated product by converting the amine to its salt by reaction of the crude liquid product with an inorganic acid followed by further treatment of the amine salt with alkali and thereafter recovering the primary amine by distillation. The oxygenated by-products of the nitration hydrogenation reactions in admixture with the unreacted paraffin separated from the amines represent a typical mixture contemplated by the instant invention which is hydrogenated to substantially pure n-paraffin.

The production of secondary alcohols from $C_6$ to $C_{30}$ n-paraffins also provides by-product streams composed of mixtures of n-paraffin and oxygenated paraffins which are according to the instant invention converted to substantially pure n-paraffin. The production of secondary alcohols from $C_6$ to $C_{30}$ paraffins is accomplished by contacting the paraffin in the liquid phase with an oxygen containing gas in the presence of boric acid at a temperature of from about 300° to 450°F. to convert from 5 to 50 weight percent of the paraffin to a mixture of alkyl borate esters, unreacted paraffin and degradation products including olefins and oxygenated products other than the borate esters. The mixture is first fractionated to separate an overhead fraction comprising unreacted n-paraffins, a portion of the by-products including such materials as olefins, ketones, some alcohols and traces of borate ester, and a bottoms fraction containing the borate ester and polyoxygenated by-products including ketoalcohols, acids, ketoacids and glycols. The bottoms are contacted with water at from 100° to 212°F. to hydrolize the borate esters to secondary alcohols which bottoms separate into two phases comprising a top organic layer containing secondary alcohol and substantially all of the polyoxygenated products and a bottom layer comprised of aqueous boric acid, which layers are separated. The organic layer is fractionated to separate desired secondary alcohols as an overhead and a bottoms comprising polyoxygenated materials. The overhead recovered by the first fractionation comprised of unreacted n-paraffins, olefin and oxygenated products including alcohols and ketones represents a typical mixture contemplated for hydrogenation according to the instant invention. All or a portion of the final organic bottoms containing the polyoxygenated by-products can also be included into the mixture contemplated for hydrogenation herein.

Another process providing mixtures of n-paraffin and oxygenated paraffins, which according to the instant invention can be substantially converted to pure n-paraffins, involves the production of normal paraffin oximes having from 6 to 30 carbon atoms from normal paraffins. The oximes are prepared by photochemically reacting and converting from 5 to 50 weight percent of a $C_6$ to $C_{30}$ normal paraffin with a gaseous nitrosating agent, such as nitrosyl halides, nitrosyl sulfuric acid, nitrogen oxide and chlorine or nitrogen peroxide and chlorine at a temperature of from about 30° to 140°F. under the influence of light to produce normal paraffin oximes and up to about 5 weight percent oxygenated by-products primarily composed of ketones. Some alkylchlorides are also formed. The oxime is thereafter converted to the sulfate and unconverted $C_6$ to $C_{30}$ paraffin, ketones and alkylchlorides are extracted using a low boiling hydrocarbon such as cyclohexane, n-pentane, isoheptane or petroleum ether. Thereafter the low boiling hydrocarbon is separated by distillation and the mixture of the n-paraffin, oxygenated paraffin, in this instance ketones, along with the alkylchlorides, can be converted to substantially pure n-paraffin according to the instant invention.

It will be appreciated that other known processes providing mixtures of n-paraffin and oxygenated paraffin by-products can be improved by applicants' catalytic hydrogenation and that the processes mentioned above are merely illustrative and are not intended to limit the instantly claimed invention.

In order to illustrate more fully the nature of our invention and manner of practicing the same, the following examples are presented. In these examples the best mode contemplated by us for carrying out our invention is set forth.

EXAMPLE I

The conversion of n-paraffins to secondary alkyl primary amines is undertaken by providing a fresh water-white $C_{10}$ to $C_{14}$ n-paraffin hydrocarbon composition having the following carbon chain length distribution on a weight percent basis: $C_{10}$ 11.1, $C_{11}$ 28.7, $C_{12}$ 32.2, $C_{13}$ 26.9, $C_{14}$ 1.1. To 10.7 weight percent of fresh normal paraffins there is mixed 89.3 weight percent of previously processed and upgraded recycle paraffins according to the instant invention.

A paraffin hydrocarbon charge at the rate of 940 pounds per hour is nitrated with 60 pounds per hour of nitrogen dioxide wherein nitration proceeds at 330°F. under a pressure of 4 p.s.i.g. Off-gases comprising paraffin, nitrogen dioxide, nitric oxide, nitrous oxide, nitrogen, carbon dioxide, carbon monoxide and water are withdrawn, the off-gases partially condensed, and condensed paraffin recycled. Nitric oxide in the overhead gas is oxidized to nitrogen dioxide, and oxidized gas cooled to condense nitrogen dioxide, and the liquefied nitrating agent recycled. Non-condensible gases including nitrogen, nitric oxide, nitrous oxide, carbon monoxide and carbon dioxide are vented.

The crude nitrated paraffin product, 977 pounds, comprising 80 weight percent n-paraffin, 14.7 weight percent nitroparaffin and 4.4 weight percent by-products including oxidized paraffin and polyfunctionals of which 0.6 weight percent are ketones, 1.2 weight percent are nitrites and 0.5 weight percent are nitrates is continuously caustic washed with about 70 pounds per hour of 10 percent aqueous sodium hydroxide in a line mixer at 200°F. and 50 p.s.i.g. The resulting aqueous layer is separated in a settler and removed. The organic layer is washed at 180°F. and 50 p.s.i.g. with 27 pounds per hour of water in a conventional countercurrent extraction tower. The washed nitrate product contains 129 pounds of nitrated paraffin and 833 pounds of n-paraffin and other materials that include 0.43 weight percent ketones, 0.95 weight percent nitrites and 0.41 weight percent nitrates.

The crude nitrated paraffin composition is hydrogenated at an average temperature of 400°F. over a hydrogenation catalyst composed of one weight percent palladium on carbon at a liquid hourly space velocity of 1.5 volumes of liquid per volume of catalyst per hour. Hydrogenation is conducted under a hydrogen pressure of 560 p.s.i.g. Following hydrogenation, essentially all of the nitroparaffin is reduced to amine. Hydrogen, ammonia and some water are removed as gases and remaining water and ammonia are decanted from the recovered crude hydrogenation product at 110°F.

The crude hydrogenation product at a rate of 950 pounds per hour comprising about 844 pounds of n-paraffins and miscellaneous by-products including secondary amines, alcohols and ketones, 90 pounds of secondary alkyl primary amine, and 16 pounds of water and ammonia, is contacted with 76 gallons of 1.5 N HCl and the mixture stirred for one hour. An additional 100 gallons of water is added and the mixture stirred. The mixture is allowed to settle yielding 789 pounds of a hydrocarbon phase and an aqueous phase containing the amine hydrochlorides along with 30 pounds of paraffin. The aqueous phase is charged with pentane, stirred and allowed to settle for 2 hours. The aqueous phase containing the amine hydrochloride is neutralized with sodium hydroxide and 115 pounds of amines and about 100 pounds of pentane are recovered. The amine-pentane mixture is stripped at atmospheric pressure at a temperature of 250°F. A total of 115 pounds of amine product is collected, vacuum distilled at 300°F. and 10 m.m. Hg and about 90 pounds of primary amines recovered as the overhead and the bottoms contain secondary amines, diamines, aminoalcohols and aminoketones.

The hydrocarbon phase, 789 pounds comprises about 99 weight percent n-paraffin and about 1 weight percent oxygenates. This stream is introduced into a hydrogenation zone at the rate of 789 pounds per hour and hydrogenated at 670°F. with 0.3 pound per hour of ethylene diamine and 16 pounds per hour of hydrogen at 500 p.s.i.g. at a liquid hourly space velocity of 1.5 in the presence of a 0.75 platinum on alumina catalyst. After separating hydrogen, ammonia and water, the hydrogenated product is essentially free of oxygenated by-products and isoparaffins and is recycled for introduction to the nitration reactor.

EXAMPLE II

An amine-depleted $C_{10}$ to $C_{14}$ paraffin stream composed of about 3 weight percent by-products including ketones and alcohols is introduced into a hydrogenation reactor containing a nickel or kieselguhr hydrogenation catalyst at the rate of 3.3 pounds per hour and hydrogenated at 610° to 615°F. with 0.03 pounds per hour of hydrogen at about 600 p.s.i.g. Sampling of the off-gas shows it to contain 7 percent methane thereby demonstrating that substantial hydrocracking has occurred.

EXAMPLE III

A continuous process for converting n-paraffin to secondary alcohols is undertaken by introducing a $C_{10}$ to $C_{14}$ n-paraffin charge composed of 12.6 weight percent fresh n-paraffin and 87.4 weight percent recycle n-paraffin hydrogenated according to this invention.

815 pounds per hour of the paraffin charge is preheated to 350°F. and introduced to two continuous stirred tank reactors in series along with orthoboric acid, the acid added at the rate of 2.1 weight percent basis total paraffin charge to each reactor for a total of 4.2 weight percent boric acid basis the total paraffin charge. Air is introduced to each reactor in the amount of 1.3 SCF per hour per pound of paraffin charge to the first reactor and at the rate of 0.7 SCF/hr./lb. to the second reactor. The reactors are operated at 10 p.s.i.g. and are each equipped with means to separate overhead by-product water. The average residence time of the paraffin in the first reactor is 3.1 hours and in the second reactor 2.6 hours, thereby providing a total conversion of paraffin to 17.1 weight percent borate esters, about 0.55 weight percent oxygenates, and about 0.1 weight percent olefins, with the remainder of the organic material being unconverted paraffin. The reactor effluent stream is first fractionated by vacuum stripping at 365°F. and 5 mm pressure to obtain a bottom stream of stripped borate esters and an overhead containing predominantly $C_{10}$ to $C_{14}$ unreacted n-paraffin, 0.2 weight percent secondary alcohols, 0.1 weight percent olefins, 0.12 weight percent acids, 0.24 weight percent ketones and 0.54 weight percent borate esters.

The bottom stream of stripped borate esters, other polyoxygenated by-products and traces of unreacted n-paraffin is contacted with water at 180°F. in an in-line mixer at a weight ratio of water to borate ester containing stream of 2:1 and a top organic layer is separated from a bottom layer composed of aqueous boric acid.

The top organic layer composed of 85 weight percent secondary alcohols, 0.6 weight percent unreacted paraffins, 1.2 weight percent boric acid and the remainder polyoxygenated paraffins is fractionated at 390°F. and 2 mm pressure to remove overhead 101 pounds of secondary alcohols of approximtely 99 percent purity. The bottoms comprising $C_{10}$ to $C_{14}$ polyoxygenated paraffins are steam stripped to form an overhead composed of 30 weight percent acids, 12 weight percent ketones, 38 weight percent glycols, 17 weight percent esters and 3 weight percent boric acid. This overhead is combined with the first fractionated overhead containing predominantly $C_{10}$ to $C_{14}$ unreacted paraffin to form a recycle stream comprising 0.1 weight percent olefin, 0.5 weight percent acids, 0.4 weight percent ketones, 0.5 weight percent glycols, 0.7 weight percent borate esters, 0.4 weight percent boric acid and the remainder unreacted paraffin.

The recycle stream is introduced through a bed of alumina at 400°F. acting as a guard chamber and thereafter introduced into a hydrogenation reactor at the rate of 719 pounds per hour and hydrogenated at 690°F. with 0.9 pounds per hour of ammonia and 25 pounds per hour of hydrogen at 800 p.s.i.g. at a liquid hourly space velocity of 2.0 in the presence of a 3 weight percent nickel oxide – 12 weight percent molybdenum on alumina catalyst. After separating hydrogen, ammonia and water, the hydrogenated product is essentially free of oxygenated by-products, the n-paraffin content is in excess of 99 weight percent and the product is recycled for introduction to the stirred tank reactors. Virtually no methane, light hydrocarbons and isoparaffins are produced during hydrogenation. For 101 pounds of 99 percent purity secondary alcohol, there is required 103 pounds of fresh n-paraffin feed in the continuous process.

EXAMPLE IV

A recycle stream similar to that in Example III is hydrogenated at 550°F. and 800 p.s.i.g. with 3.5 pounds of hydrogen per 100 pounds of recycle feed over a nickel on kieselguhr hydrogenation catalyst at a liquid hourly space velocity of 2.0. About 12 weight percent of the feed is converted to paraffins lighter than $C_6$. For 101 pounds of 99 percent purity secondary alcohol, there is required 115 pounds of fresh n-paraffin feed in the continuous process employing the catalytic hydrogenation described in this example. It will be seen that the claimed invention employing the catalyst illustrated in Example III is more selective in converting the mixture to n-paraffin than the conventional hydrogenation catalyst employed in Example IV.

We claim:

1. In a process for producing secondary alkyl primary amines from n-paraffins wherein a portion of said n-paraffin is nitrated to form a nitroparaffin along with nitrated and oxygenated by-products, wherein said nitroparaffin is essentially completely hydrogenated to said amine and where said amine is separated from a mixture of unreacted paraffin and oxygenated by-products, the improvement which comprises:

a. catalytically hydrogenating said mixture at a temperature of from about 600° to 750°F. in the presence of a catalyst composed of alumina and a Group VIII metal and from about 10 to 5000 parts per million of nitrogen introduced as ammonia or an organonitrogen compound selected from the group consisting of monoalkylamines, dialkylamines, trialkylamines, nitriles and alkenylpolyamines basis said paraffin mixture; and b. recycling said hydrogenated product of (a) for nitration with said n-paraffin.

2. A process according to claim 1 wherein said paraffin and oxygenated by-product have from 6 to 30 carbon atoms.

3. A process according to claim 1 wherein said Group VIII metal is platinum, palladium, rhodium, ruthenium, nickel or cobalt and where said metal is present in an amount of from about 0.1 to 5.0 weight percent based on said catalyst.

4. A process according to claim 1 wherein said nitrogen is present as ammonia.

5. A process according to claim 1 wherein from 100 to 3000 parts per million of nitrogen are present.

6. A process according to claim 1 wherein said organonitrogen compound is ethylene diamine.

7. A process according to claim 1 wherein said organonitrogen compound is isopropylamine.

8. A process according to claim 1 wherein said organonitrogen compound is acetonitrile.

9. A process according to claim 1 wherein said organonitrogen compound is methylamine.

10. A process according to claim 1 wherein said temperature is from 610° to 700°F.

11. A process according to claim 1 wherein said mixture is additionally and subsequently hydrogenated at from about 450° to 650°F.

* * * * *